(12) United States Patent
Majka et al.

(10) Patent No.: US 7,919,515 B2
(45) Date of Patent: Apr. 5, 2011

(54) 3-PHENYLPROPIONIC ACID DERIVATIVES

(75) Inventors: Zbigniew Majka, Lubzina (PL); Katarzyna Ewa Rusin, Warsaw (PL); Andrzej Wojciech Sawicki, Jozefow (PL); Krzysztof Kurowski, Siedlce (PL); Katarzyna Joanna Matusiewicz, Lwowek Slaski (PL); Tomasz Stawinski, Wiazowna (PL); Daniel Sulikowski, Gubin (PL)

(73) Assignee: Adamed Sp. z o.o., Czosnow K/Warsawy (PL)

( * ) Notice: Subject to any disclaimer, the term of this patent is extended or adjusted under 35 U.S.C. 154(b) by 779 days.

(21) Appl. No.: 11/740,820

(22) Filed: Apr. 26, 2007

(65) Prior Publication Data
US 2007/0219259 A1    Sep. 20, 2007

Related U.S. Application Data

(62) Division of application No. 11/298,920, filed on Dec. 8, 2005, now Pat. No. 7,312,338.

(30) Foreign Application Priority Data

Dec. 20, 2004    (PL) .......................................... 371841

(51) Int. Cl.
*A61K 31/423* (2006.01)
(52) U.S. Cl. ...................................................... 514/375
(58) Field of Classification Search .................. None
See application file for complete search history.

(56) References Cited

U.S. PATENT DOCUMENTS

| | | | |
|---|---|---|---|
| 5,296,486 | A | 3/1994 | Lazer et al. |
| 6,838,453 | B2 | 1/2005 | Demassey et al. |
| 2006/0160868 | A1 | 7/2006 | Majka et al. |
| 2006/0160870 | A1 | 7/2006 | Majka et al. |
| 2007/0088061 | A1 | 4/2007 | Majka et al. |

FOREIGN PATENT DOCUMENTS

| | | |
|---|---|---|
| EP | 1184366 | 3/2002 |
| JP | 58125039 | 7/1983 |
| WO | WO-95/25107 | 9/1995 |
| WO | 97/31907 | 9/1997 |
| WO | 01/17994 | 3/2001 |
| WO | 01-85729 | 11/2001 |
| WO | 03/011814 | 2/2003 |
| WO | 03/011834 | 2/2003 |

OTHER PUBLICATIONS

Takano et al., Circulation Journal, vol. 73, Feb. 2009, pp. 214-220.*
Auwerx, American Journal of Physiology, Gastrointestinal and Liver Physiology, Apr. 2002, 282(4), pp. G581-G585.*
Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*
Curtis et al., The Journal of the American Board of Family Practice, vol. 18, pp. 37-43, (2005).*
J. L. Collins et al., "N-(2-Benzoylphenyl)- L-Tyrosine PPARgamma Agonists. 2. Structure-Activity Relationship and Optimization of the PhenylAlkyl Ether Moiety;", J. Med. Chem. vol. 41, pp. 5037-5054, (1998). XP-002211273.
J. E. Cobb et al., "N-(2-Benzoylphenyl)-L-Tyrosine PPARgamma Agonists. 2. Structure-Activity Relationship and Optimization of the N-Aryl Substituent", J. Med. Chem. vol. 41, pp. 5055-5069 (1998). XP-002156427.
Lazer et al., Journal of Medicinal Chemistry, 37(7), pp. 913-923 (1994).
J. Rudolph, "Facile Access to N-Thiazolyl Alpha-Amino Acids From Alpha-Bromo Ketone and Alpha-Amino Acids", Tetrahedron, vol. 56m 3161-3165 (2000).

\* cited by examiner

*Primary Examiner* — Laura L. Stockton
(74) *Attorney, Agent, or Firm* — Fish & Richardson P.C.

(57) ABSTRACT

The invention relates to new compounds, being 3-phenylpropionic acid derivatives of formula I wherein W represents COOH group or its bioisosters, or —COO—$C_1$-$C_4$-alkyl group; Y represents NH, N—$C_1$-$C_{10}$-alkyl, O, or S; Z represents NH, N—$C_1$-$C_{10}$-alkyl, N-aryl, N-heteroaryl, S, or O; X represents O, S, NH, N—$C_1$-$C_{10}$-alkyl, N-aryl, $NSO_2$—$C_1$-$C_{10}$-alkyl, N—$SO_2$-aryl, or N—$SO_2$-heteroaryl; $R_1$ to $R_8$ each independently represent hydrogen atom or a substituent defined in the description; A is as defined in the description; n represents an integer from 0 to 4, inclusive; and pharmaceutically acceptable salts thereof. The compounds are the ligands of PPAR-gamma receptor and are useful as medicaments.

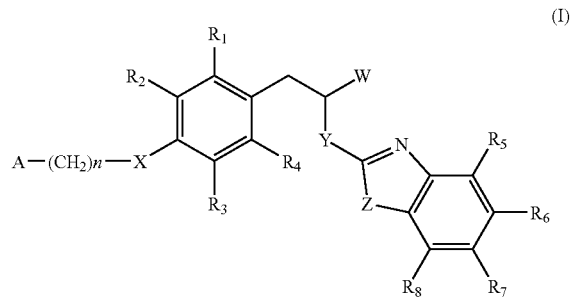

(I)

27 Claims, No Drawings

3-PHENYLPROPIONIC ACID DERIVATIVES

This application is a divisional of U.S. patent application No. 11/298,920, filed Dec. 8, 2005, now U.S. Pat. No. 7,312, 338 which claims priority to Polish Patent Application No. P 371841, filed Dec. 20, 2004, which is incorporated by reference herein in its entirety.

This application claims the benefit of Polish Patent Application No. P-371841, filed Dec. 20, 2004, which is herein incorporated by reference in its entirety.

FIELD OF THE INVENTION

The present invention relates to new compounds, being 3-phenylpropionic acid derivatives, pharmaceutical compositions comprising the same, and their use for the treatment and/or prevention of peroxysome proliferator-activated receptor gamma (PPARγ) mediated diseases and conditions. The compounds show the ability to bind to PPARγ receptor and modify its activity.

THE STATE OF THE ART

More than 20 years ago, the thiazolidinedione group of compounds was discovered, showing the activity in rodent models of type 2 diabetes and insulin resistance. Although their mechanism of action was not known, the compounds have been successfully used in therapy of type 2 diabetes. Publications demonstrating that they exerted their effect via the nuclear PPAR gamma receptor were published only in the middle of 90's. Now, it is well known that intracellular receptor proteins of the PPAR family control the expression of genes involved in the regulation of lipid-carbohydrate metabolism.

Diseases such as hyperlipidemia, atherosclerosis, obesity, and type 2 diabetes become the serious concern not only for developed industrial societies. It is estimated that more than 150 million people worldwide suffer from type 2 diabetes, and this number is expected to double by 2025. In Poland, currently about 2 million people suffer from this disease, and the same number is at risk of developing it. Costs of medical care in diabetic patients reach 6 to 8 percent of total medical care budgets. At the initial stage, diabetes can be symptomless, and may begin at any age; however, most often occurs at middle age and in elderly persons. The progress of type 2 diabetes is a result of overlapping of physiological disorders such as: tissue insulin resistance, insufficient pancreatic insulin production, elevated insulin production following intensified gluconeogenesis. Most often diabetic complications are microvascular changes in the retina, kidneys and nervous system, what leads to increased risk of blindness, renal insufficiency and neuropathy. Diabetes is also the main causative factor of heart infarct and brain stroke.

PPARγ receptors, belonging to the family of nuclear receptors, play the role in the regulation of lipid metabolism and storage. They are expressed in adipose tissue and large intestine, and are involved in the lipogenesis process. Ligands activating PPARγ receptor can enhance insulin effect and lower the plasma glucose level. They can be also useful in the management and therapy of lipid metabolism and energy balance disorders.

There are known compounds being L-tyrosine derivatives or analogues, which exert their action via modulation of the PPARγ receptor response, thus acting on the glucose metabolism, lipid hemostasis and energy balance.

In the international patent applications Nos. WO03/011834 and WO03/011814 there are disclosed N-(2-benzoylphenyl)-L-tyrosine derivatives, which have a partial PPARγ agonist activity and may be useful in the treatment and prophylaxis of inter alia impaired insulin tolerance, type 1 and 2 diabetes, dyslipidemia, disorders associated with syndrome X, such as hypertension, obesity, insulin resistance, hyperglycemia, atherosclerosis, myocardial ischemia, coronary heart disease, renal diseases, as well as for improving cognitive functions and for treating diabetic complications. The disclosed compounds represent L-tyrosine derivatives wherein tyrosine hydroxyl group is substituted with vinyl group and nitrogen in tyrosine amino group is substituted with 2-benzoylphenyl group.

In the international patent application No. WO01/17994 there are disclosed oxazole compounds as PPARγ antagonists, which may be useful in the treatment of diabetes, obesity, metabolic syndrome, impaired insulin tolerance, syndrome X and cardiovascular diseases, including dyslipidemia. The compounds represent L-tyrosine derivatives wherein tyrosine carboxyl group is substituted with a 5-membered heterocyclic group, tyrosine hydroxyl group is substituted with (5-methyl-2-phenyloxazol-4-yl)ethyl group, and nitrogen in tyrosine amino group is substituted with 2-benzoylphenyl group.

In the international patent application No. WO97/31907 there are disclosed 4-hydroxyphenylalcanoic acid derivatives with agonistic activity to PPARγ. Among others, there are disclosed L-tyrosine derivatives wherein tyrosine hydroxyl group is substituted with a 5-membered heterocyclic group, which itself can be substituted, and nitrogen in tyrosine amino group is substituted with 2-substituted phenyl group, including 2-benzoylphenyl group.

In the art still exists a need for new compounds—ligands of PPARγ, which may be useful in the treatment and/or prophylaxis of diabetes and complications resulting from or associated with diabetes, especially lipid metabolism disorders and cardiovascular diseases.

THE SUMMARY OF THE INVENTION

The present invention relates to new compounds, 3-phenylpropionic acid derivatives of formula (I)

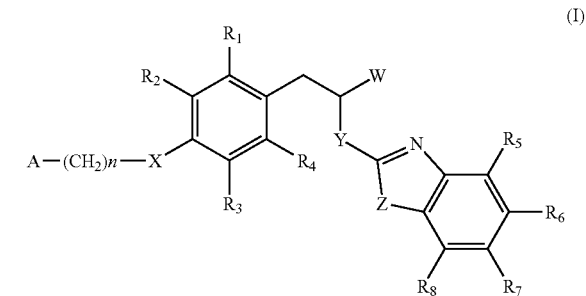

wherein:
W represents COOH group or its bioisosters, or —COO—$C_1$-$C_4$-alkyl group;
Y represents NH, N—$C_1$-$C_{10}$-alkyl, O, or S;
Z represents NH, N—$C_1$-$C_{10}$-alkyl, N-aryl, N-heteroaryl, S, or O,
X represents O, S, NH, N—$C_1$-$C_{10}$-alkyl, N-aryl, $NSO_2$—$C_1$-$C_{10}$-alkyl, N—$SO_2$-aryl, or N—$SO_2$-heteroaryl;
$R_1$, $R_2$, $R_3$, $R_4$, $R_5$, $R_6$, $R_7$ and $R_8$ each independently represents hydrogen atom or a substituent selected from the group consisting of:

$C_1$-$C_4$-alkyl, $C_1$-$C_4$-alkoxy, $C_3$-$C_7$-cycloalkyl, $C_3$-$C_7$-cycloalkoxy, $C_1$-$C_4$-thioalkoxy, $C_3$-$C_7$-cyclothioalkoxy, halogen atom, halogen-substituted $C_3$-$C_7$-cycloalkyl, aryl, heteroaryl, —$NO_2$, —CN, —$SO_2$—$NH_2$, —$SO_2$—NH—$C_1$-$C_4$-alkyl, —$SO_2$—N($C_1$-$C_4$-alkyl)$_2$, —CO—$C_1$-$C_4$-alkyl, —O—CO—$C_1$-$C_4$-alkyl, —CO—O—C, —$C_4$-alkyl, —CO-aryl; —CO—$NH_2$, —CO—NH—C, —$C_4$-alkyl, —CO—N($C_1$-$C_4$-alkyl)$_2$;

A represents $C_1$-$C_4$-alkyl, $C_3$-$C_7$-cycloalkyl, halogen-substituted $C_3$-$C_7$-cycloalkyl, aryl, heteroaryl, heterocyclyl, —NH—CO—$C_1$-$C_4$-alkyl, —N($C_1$-$C_4$-alkyl)-CO—$C_1$-$C_4$-alkyl, —NH—CO-aryl, —N($C_1$-$C_4$-alkyl)-CO-aryl, —N($C_1$-$C_4$-alkyl)-CO—$C_3$-$C_7$-cycloalkyl, —NH—CO—$NH_2$, —NH—CO—NH—$C_1$-$C_4$-alkyl, —NH—CS—NH—$C_1$-$C_4$-alkyl, —NH—CO—NH-aryl, —NH—CS—NH-aryl, —$SO_2$-$C_1$-$C_4$-alkyl, —$SO_2$-aryl, or —$SO_2$-heteroaryl; wherein aryl, heteroaryl and heterocyclyl are optionally substituted with one or more substituents independently selected from the group consisting of $C_1$-$C_4$-alkyl, $C_1$-$C_4$-alkoxy, $C_1$-$C_4$-thioalkoxy, ethylenedioxy, CN, halogen or phenyl, said phenyl being optionally substituted with one or more substituents independently selected from $C_1$-$C_4$-alkyl, $C_1$-$C_4$-alkoxy and halogen atom; and n represents an integer from 0 to 4, inclusive; and and pharmaceutically acceptable salts thereof.

One group of compounds of the invention comprises those compounds wherein W represents COOH.

Another group of compounds of the invention comprises those compounds wherein Y represents NH.

Another group of compounds of the invention comprises those compounds wherein Y represents O.

Another group of compounds of the invention comprises those compounds wherein Y represents N—$C_1$-$C_4$-alkyl, especially N—$CH_3$.

Still another group of compounds of the invention comprises those compounds wherein Z represents O.

Still another group of compounds of the invention comprises those compounds wherein Z represents S.

Still another group of compounds of the invention comprises those compounds wherein Z represents N—$C_1$-$C_4$-alkyl, especially N—$CH_3$.

Still another group of compounds of the invention comprises those compounds wherein Z represents N-phenyl.

Still another group of compounds of the invention comprises those compounds wherein X represents O.

Still another group of compounds of the invention comprises those compounds wherein X represents S.

Still another group of compounds of the invention comprises those compounds wherein X represents $NSO_2$—$C_1$-$C_4$-alkyl, especially $NSO_2$—$CH_3$.

Still another group of compounds of the invention comprises those compounds wherein W represents COOH, Y represents NH, Z represents O and X represents O.

Still another group of compounds of the invention comprises those compounds wherein W represents COOH, Y represents O, Z represents O, and X represents O.

Still another group of compounds of the invention comprises those compounds wherein W represents COOH, Y represents NH, Z represents O, and X represents $NSO_2$—$C_1$-$C_4$-alkyl, especially $NSO_2$—$CH_3$.

Still another group of compounds of the invention comprises those compounds wherein W represents COOH, Y represents NH, Z represents S, and X represents $NSO_2$—$C_1$-$C_4$-alkyl, especially $NSO_2$—$CH_3$.

A particular embodiment of the compounds of formula (I) as defined above are those compounds wherein each of $R_1$ to $R_8$ represents hydrogen atom.

Another particular embodiment of the compounds of formula (I) as defined above are those compounds wherein n is equal to 1 or 2.

Another group of compounds of the invention comprises those compounds wherein A represents heterocyclyl, said heterocyclyl being optionally substituted with one or more substituents independently selected from the group consisting of $C_1$-$C_4$-alkyl, $C_1$-$C_4$-alkoxy, $C_1$-$C_4$-thioalkoxy, CN, halogen atom, and phenyl.

Within the above group, A preferably represents isoxazolyl, optionally substituted with one or more substituents independently selected from $C_1$-$C_4$-alkyl, especially —$CH_3$.

Further group of compounds of the invention comprises those compounds wherein A represents phenyl, said phenyl being optionally substituted, especially with ethylenedioxy group.

Further group of compounds of the invention comprises those compounds wherein A represents —N($C_1$-$C_4$-alkyl)-CO—$C_3$-$C_7$-cycloalkyl, especially —N($CH_3$)—CO-cyclohexyl.

Further group of compounds of the invention comprises those compounds wherein A represents —N($C_1$-$C_4$-alkyl)-CO-heteroaryl wherein heteroaryl is optionally substituted with one or more substituents independently selected from the group consisting of $C_1$-$C_4$-alkyl, $C_1$-$C_4$-alkoxy, $C_1$-$C_4$-thioalkoxy, CN, halogen atom, phenyl, and phenyl optionally substituted with one or more substituents independently selected from the group consisting of $C_1$-$C_4$-alkyl, $C_1$-$C_4$-alkoxy, and halogen atom.

A preferred heteroaryl is pyrimidinyl, optionally substituted with one or more substituents independently selected from the group consisting of $C_1$-$C_4$-alkyl, $C_1$-$C_4$-alkoxy, halogen atom, phenyl, and phenyl optionally substituted with one or more substituents independently selected from the group consisting of $C_1$-$C_4$-alkyl, $C_1$-$C_4$-alkoxy, and halogen atom.

As examples of specific compounds of the invention, the following can be mentioned:

1. (2S)-2-(1,3-benzoxazol-2-ylamino)-3-[4-(2,3-dihydro-1,4-benzodioxin-6-ylmethoxy)phenyl]propionic acid,
2. (2S)-2-(1,3-benzoxazol-2-ylamino)-3-[4-((3,5-dimethylisoxazol-4-yl)-methoxy)phenyl]propionic acid,
3. (2S)-2-(1,3-benzoxazol-2-ylamino)-3-[4-(2-[(cyclohexylcarbonyl)-(methyl)amino]ethoxy)phenyl]propionic acid,
4. (2S)-2-(1,3-benzoxazol-2-ylamino)-3-[4-(2-[5-methyl-2-(3,4,5-trimethoxyphenyl)-1,3-oxazol-4-yl]ethoxy)phenyl]propionic acid,
5. (2S)-2-(1,3-benzoxazol-2-ylamino)-3-[4-(4-{2-[[6-(2-chlorophenyl)-5-cyano-2-(methylthio)pyrimidin-4-yl](methyl)amino]ethoxy})phenyl]-propionic acid,
6. (2S)-2-(1,3-benzoxazol-2-ylamino)-3-[4-(2-(2-tert-butyl-5-methyl-1,3-oxazol-4-yl)ethoxy)phenyl]propionic acid,
7. (2S)-2-(1,3-benzoxazol-2-ylamino)-3-[4-(2-(2-tert-butyl-5-methyl-1,3-oxazol-4-yl)ethoxy)phenyl]propionic acid,
8. (2S)-2-(1,3-benzoxazol-2-ylamino)-3-[4-(2-[(cyclohexylcarbonyl)-(methyl)amino]thioethoxy)phenyl]propionic acid,
9. (2S)-2-(1,3-benzoxazol-2-ylamino)-3-[4-(2-[(cyclohexylcarbonyl)-(methyl)amino]ethylmethanesulfonylamino)phenyl]propionic acid, and 10. (2S)-2-(1,3-benzoxazol-2-yloxy)-3-[4-(2-[(cyclohexylcarbonyl)(methyl)-amino]ethoxy)phenyl]propionic acid, and pharmaceutically acceptable salts thereof.

The compounds of the invention have high affinity to the peroxisome proliferator-activated receptor gamma (PPARγ). Thus the compounds demonstrate the ability to bind to the PPARγ and to modulate its activity.

The invention relates also to a pharmaceutical composition comprising at least one compound of formula (I) as defined above or a pharmaceutically acceptable salt thereof, optionally in combination with other pharmacologically active ingredient, together with one or more pharmaceutically acceptable carriers and/or excipients.

The invention relates also to a compound of formula (I) as defined above for use as a medicament.

The invention further relates to the use of a compound of formula (I) as defined above or a pharmaceutically acceptable salt thereof for the preparation of a medicament for the treatment and/or prophylaxis of diseases and conditions mediated by peroxisome proliferator-activated receptor gamma (PPARγ).

The invention further relates to a method of treatment and/or prophylaxis of diseases and conditions mediated by peroxysome proliferator-activated receptor gamma (PPARγ) in a mammal subject in need thereof, said method comprising administration to said mammal a compound of formula (I) as defined above in a therapeutically or prophylactically effective amount.

Such PPARγ-mediated diseases and conditions include in particular impaired insulin tolerance, insulin resistance, type 1 and type 2 diabetes, complications resulting from or associated with diabetes, such as peripheral neuropathy, renal insufficiency, retinopathy, dyslipidemia, syndrome X associated disorders, such as hypertension, obesity, hyperglycemia, atherosclerosis, myocardial ischemia, coronary heart disease, and other cardiovascular diseases, and renal diseases.

The compounds of the invention can be also useful for improving cognitive functions.

DETAILED DISCLOSURE OF THE INVENTION

Definitions

The term, "bioisoster" as used herein relates to a chemical moiety, which replaces another moiety in a molecule of an active compound without significant influence on its biological activity. Other properties of the active compound, such as for example its stability as a medicament, can be affected in this way.

As bioisoster moieties for carboxy (COOH) group can be mentioned especially 5-membered heterocyclic groups having from 1 to 4 heteroatoms selected from nitrogen, oxygen and sulphur, such as for example 1,3,4-oxadiazolyl, 1,2,3-oxadiazolyl, 1,2,5-oxadiazolyl, 1,2,4-oxadiazolyl, 1,3,4-thiadiazolyl, 1,2,4-thiadiazolyl, 1,2,3-thiadiazolyl, 1,2,5-thiadiazolyl, furyl, thienyl, pyrrolyl, pyrazolyl, imidazolyl, isoxazolyl, isothiazolyl, and N-substituted tetrazolyl. 5-Membered heterocyclic groups can be optionally substituted with 1 or 2 substituents selected from the group comprising phenyl, pyridinyl, straight or branched alkyl group, amino group, hydroxy group, fluoro, chloro, bromo, iodo, trifluoromethyl, trifluoromethoxy, trifluorothiomethoxy, alkoxy, and thioalkoxy.

As bioisoster moieties for carboxy (COOH) group can be also mentioned phenyl and 6-membered heterocyclic groups having from 1 to 4 heteroatoms selected from nitrogen, oxygen and sulphur, such as for example pyridyl, pyridinyl, pyrazinyl, pyridazinyl, pyrimidinyl, triazinyl, tetrazinyl, and others. Phenyl and 6-membered heterocyclic groups can be optionally substituted with 1 or 2 substituents selected from the group comprising phenyl, pyridinyl, straight or branched alkyl group, amino group, hydroxy group, fluoro, chloro, bromo, iodo, trifluoromethyl, trifluoromethoxy, trifluorothiomethoxy, alkoxy, and thioalkoxy.

The term "halogen" relates to an atom selected from F, Cl, Br and I.

The term "alkyl" relates to a saturated, straight or branched hydrocarbon group, having indicated number of carbon atoms. As specific alkyl substituents, the following can be mentioned: methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, and decyl.

The term "aryl" relates to a mono- or bicyclic aromatic group, having from 6 to 14 carbon atoms. The examples of aryl groups are phenyl, tolyl, xylyl, naphthyl, such as naphth-1-yl, naphth-2-yl, 1,2,3,4-tetrahydronaphth-5-yl, and 1,2,3,4-tetrahydronaphth-6-yl.

The term "heteroaryl" relates to a mono- or bicyclic heteroaromatic group, having from 5 to 13 carbon atoms and 1 to 4 heteroatoms selected from N, O, and S. The examples of heteroaryl groups are pyrrol-1-yl, pyrrol-2-yl, pyrrol-3-yl, furyl, thienyl, imidazolyl, oxazolyl, thiazolyl, isoxazolyl, 1,2,4-triazolyl, oxadiazolyl, thiadiazolyl, tetrazolyl, pyridinyl, pyrimidinyl, 1,3,5-triazinyl, indolyl, benzo[b]furyl, benzo[b]thienyl, indazolyl, benzimidazolyl, azaindolyl, cynnolyl, isoquinolinyl, and carbazolyl.

The term "cycloalkyl" relates to a saturated or partially unsaturated cyclic hydrocarbon group, having from 3 to 7 carbon atoms. The examples of cycloalkyl groups are cyclopropyl, cyclobutyl, cyclopentyl, cyclopentenyl, cyclopentadienyl, cyclohexyl, cyclohexenyl, and cycloheptyl.

The term "heterocyclyl" relates to a saturated or partially unsaturated 5- to 6-membered cyclic hydrocarbon group, having from 1 to 4 heteroatoms, selected from N, O and S. Preferred saturated or partially unsaturated cyclic hydrocarbon is monocyclic and includes 4 or 5 carbon atoms and 1 to 3 heteroatoms. The examples of heterocyclyl groups are piperidinyl, piperazinyl, morpholinyl, and pyrrolidinyl.

The compounds of the invention possess chiral center at the carbon atom bearing W group and can exist in the form of the respective enantiomers, enantiomer mixtures as well as racemic mixtures.

Therefore, the R and S enantiomers, enantiomer mixtures as well as racemic mixtures of the compounds of formula (I) form the part of the invention.

Thus in one specific embodiment, the invention relates to compounds of formula (I) having the stereochemical configuration such as shown in formula (IA):

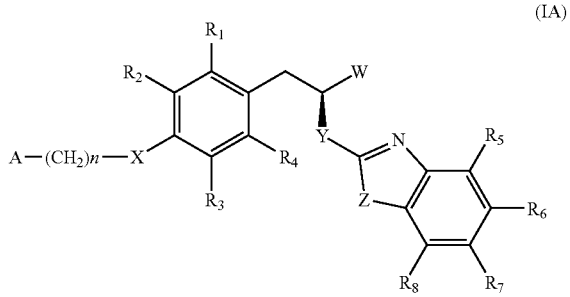

(IA)

wherein W, X, Y, Z, A, n, and $R_1$ to $R_8$ have the same meanings as defined above for formula (I), and pharmaceutically acceptable salts thereof.

In the second specific embodiment, the invention relates to compounds of formula (I) having the stereochemical configuration such as shown in formula (IB):

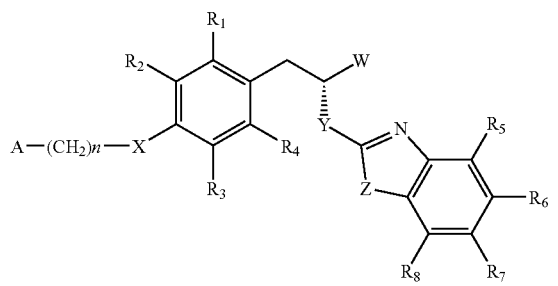

(IB)

wherein W, X, Y, Z, A, n, and $R_1$ to $R_8$ have the same meanings as defined above for formula (I),
and pharmaceutically acceptable salts thereof.

The compounds of formula (I), bearing a basic group, can be converted into salts with inorganic or organic acids in a conventional and known manner, by the treatment with suitable acid in organic solvent, such as alcohol, ketone, ether or chlorinated solvent, and the recovery of a salt in a conventional manner. Examples of such salts are those with pharmaceutically acceptable inorganic or organic acids. As examples of inorganic acid salts hydrochloride, hydrobromide, nitrate, sulfate, hydrogensulfate, pyrosulfate, sulfite, pyrosulfite, phosphate, monohydrogenphosphate, dihydrogenphosphate, metaphosphate, and pyrophosphate, can be mentioned. As examples of organic acid salts acetate, propionate, acrylate, 4-hydroxybutyrate, caprylate, capronate, decanoate, oxalate, malonate, succinate, glutarate, adipate, pimelate, maleate, fumarate, citrate, tartrate, lactate, phenylacetate, mandelate, sebacate, suberate, benzoate, phthalate, alkyl- and arylsulfonates, such as methanesulfonate, propanesulfonate, p-toluenesulfonate, xylenesulfonate, salicylate, cinnamate, glutamate, aspartate, glucuronate, and galacturonate can be mentioned.

The compounds of formula (I) bearing an acidic group can be converted into salts with inorganic or organic base in a conventional and known manner by the reaction of a compound of formula (I) with suitable organic or inorganic base. Salts with pharmaceutically acceptable bases include alkaline or alkaline earth metal salts, such as Li, Na, K, Mg or Ca, ammonium salts, and salts with basic organic compounds, such as for example arginine, histidine, piperidine, morpholine, piperazine, ethylenediamine or triethylamine, as well as quaternary ammonium salts.

The present invention relates also to pharmaceutical compositions, comprising a compound of formula (I) with pharmaceutical excipients, depending on the selected route of administration.

One of the embodiments of the invention are pharmaceutical compositions suitable for oral administration. Pharmaceutical compositions suitable for oral administration can be in the form of tablets, capsules, pills, lozenges, powders or granules, or solutions or dispersions in a liquid, or similar. Each of said forms will comprise a predetermined amount of a compound of the invention as an active ingredient. The composition in the form of a tablet can be prepared employing any pharmaceutical excipients known in the art for that purpose, and conventionally used for the preparation of solid pharmaceutical compositions. The examples of such excipients are starch, lactose, microcrystalline cellulose, magnesium stearate and binders, for example polyvinylpyrrolidone. Furthermore, an active compound can be formulated as controlled-release preparation, such as tablets comprising hydrophilic or hydrophobic matrix.

Pharmaceutical composition in the form of a capsule can be formulated using conventional procedures, for example by incorporation of a mixture of an active compound and excipients into hard gelatin capsules. Alternatively, a semi-solid matrix of an active compound and high molecular weight polyethylene glycol can be formed and filled into hard gelatin capsules, or soft gelatin capsules can be filled with a solution of an active compound in polyethylene glycol or dispersion thereof in an edible oil. Powder forms for reconstitution before use (for example lyophilized powders) are also contemplated. Alternatively, oily vehicles for injection formulation can be used as well.

Liquid forms for parenteral administration may be formulated for administration by injection or continuous infusion.

Accepted routes of administration by injection are intravenous, intraperitoneal, intramuscular and subcutaneous, intravenous injections being usually preferred. A typical composition for intravenous injection comprises a sterile isotonic aqueous solution or dispersion, including, for example, an active compound and dextrose or sodium chloride. Other examples of suitable excipients are lactated Ringer solution for injections, lactated Ringer solution for injections with dextrose, Normosol-M with dextrose, acylated Ringer solution for injections. The injection formulation can optionally include a co-solvent, for example polyethylene glycol, chelating agent, for example ethylenediaminotetraacetic acid; stabilizing agent, for example cyclodextrin; and antioxidant, for example sodium pyrosulfate.

A dosage administered will depend on the patient condition and selected route of administration, and will be adjusted by the physician.

The compounds of the invention can be prepared using the processes described below and exemplified in the Examples.

Compounds of formula (I) wherein W has the meaning other than —COOH or —COO—$C_1$-$C_4$-alkyl, can be prepared by substitution of hydrogen atom at X in a compound of formula (II) with A($CH_2$)$_n$— group

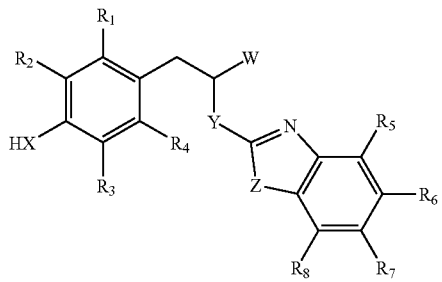

(II)

where X, Y, Z, A, n, and $R_1$ to $R_8$ have the meanings as defined for formula (I) above, and W has the meaning other than —COOH or —COO—$C_1$-$C_4$-alkyl.

Said substitution can be performed by means of Mitsunobu reaction of the compound of formula (II) as defined above with a compound of formula A($CH_2$)$_n$—OH wherein A and n have the meanings as defined above, according to the scheme 1:

Scheme 1

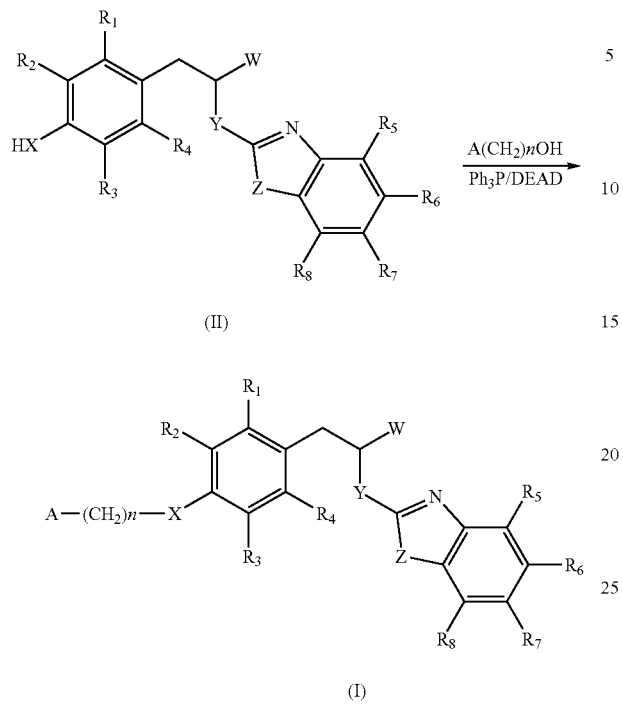

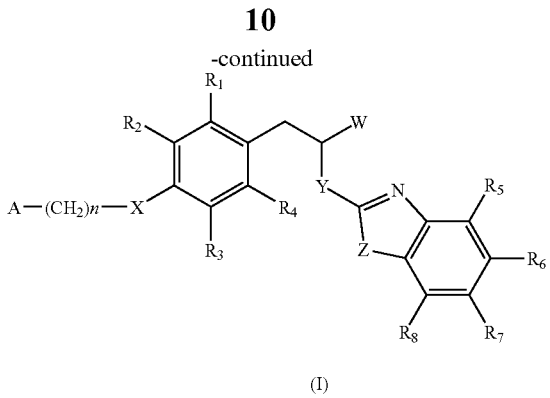

Mitsunobu reaction can be carried out in anhydrous solvents such as ether or halogenated alkane, in the presence of diazo compounds such as DEAD, DIAD, ADDP, and triphenylphosphine, typically at −20 to 20° C.

Alternatively, said substitution of hydrogen atom at X can be performed by alkylating a compound of formula (II) wherein X, Y, Z, and $R_1$ to $R_8$ have the meanings as defined for formula (I) above, and W has the meaning other than —COOH or —COO—$C_1$-$C_4$-alkyl, with a compound of formula $A(CH_2)_n$—V wherein A and n have the meanings as defined above for formula (I), and V represents a leaving group selected from halogens and alkylsulfonyl or arylsulfonyl groups, in the presence of a strong base capable of generating the anion from the compound (II), such as for example sodium hydride, to form a compound of formula (I), according to the scheme 2:

Scheme 2

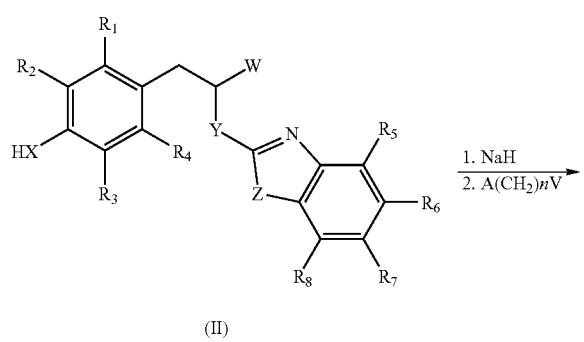

Alkylation reaction can be performed in an inert organic solvent, such as anhydrous DMF, THF, DMSO. The strong base capable of generating the anion can be sodium hydride. Sodium hydride can be used dry or as a suspension in mineral oil. Generating of the anion is carried out at room temperature until the completion of the evolution of hydrogen. Then in the second stage the alkylating agent $A(CH_2)_n$—V is added, neat or as a solution in an inert organic solvent such as DMF, THF, DMSO. The second step of alkylation can be carried out at 0 to 100° C.

The compounds of the invention of formula (I) wherein W represents —COOH or —COO—$C_1$-$C_4$-alkyl, and X, Y, Z, A, n, and $R_1$ to $R_8$ have the meanings as defined above for formula (I), can be prepared by:

a) a substitution of hydrogen atom at X with $A(CH_2)_n$— group in a compound of formula (III)

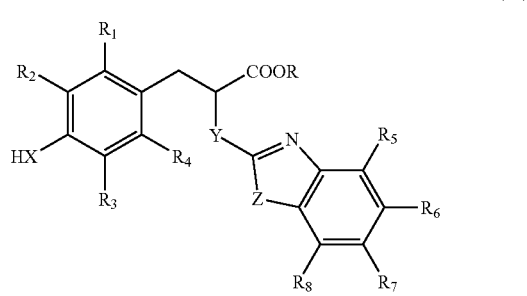

wherein R represents $C_1$-$C_4$ alkyl group, and X, Y, Z, and $R_1$ to $R_8$ have the meanings as defined for formula (I) above, to form a compound of formula (I) wherein W represents an ester group —COOR wherein R represents a $C_1$-$C_4$ alkyl group, and X, Y, Z, A, n, and $R_1$ to $R_8$ have the meanings as defined for formula (I) above, followed by b) optionally, a basic hydrolysis of the ester group —COOR to —COOH group, to form a compound of formula (I) wherein W represents —COOH.

Said substitution in step a) can be performed by Mitsunobu reaction of a compound of formula (III) with a compound of formula $A(CH_2)_n$—OH wherein A and n have the meanings as defined above for formula (I), to form a compound of formula (IV), according to the scheme 3:

Scheme 3

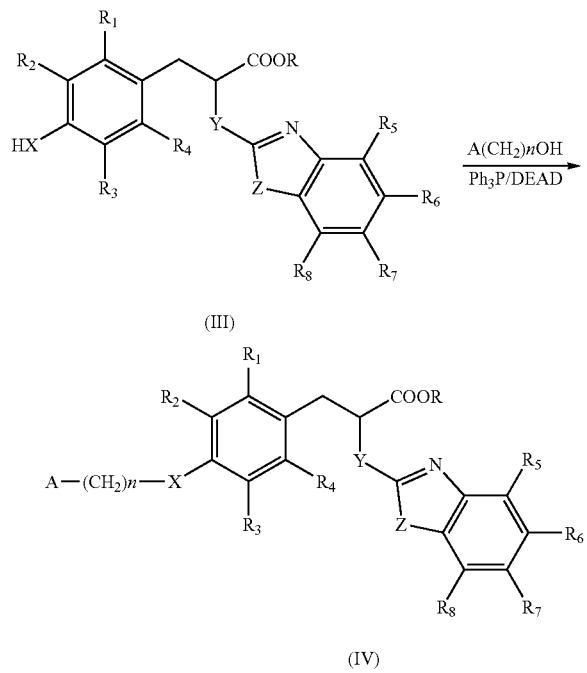

Scheme 4

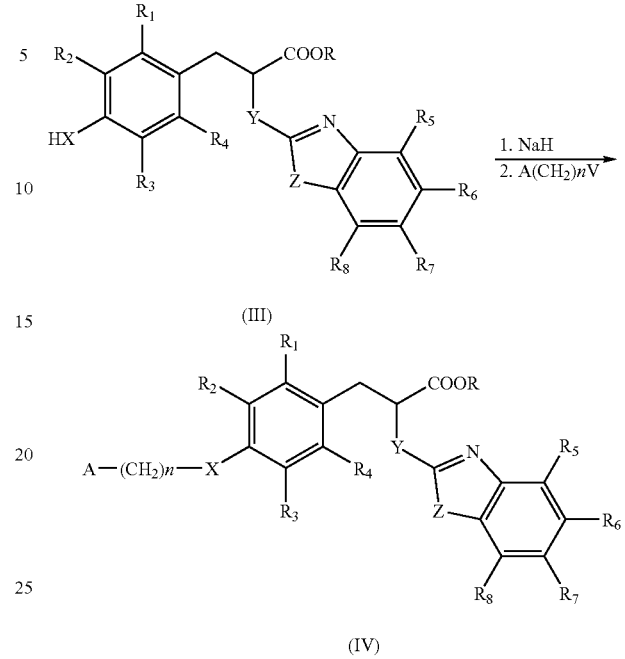

Mitsunobu reaction can be carried out as described above, in anhydrous solvents such as ether or halogenated alkane, in the presence of diazo compounds such as DEAD, DIAD, ADDP, and triphenylphosphine, usually at −20 to 20° C.

Alternatively, said substitution of hydrogen atom at X can be carried out by reacting a compound of formula (III) wherein R represents $C_1$-$C_4$ alkyl, and X, Y, Z, and $R_1$ to $R_8$ have the meanings as defined for formula (I) above, with a compound of formula $A(CH_2)_n$—V wherein $A(CH_2)_n$— has the meaning as defined above for formula (I), and V represents a leaving group selected from halogens and alkylsulfonyl or arylsulfonyl groups, in the presence of a strong base capable of generating an anion from the compound (III), such as sodium hydride, to form a compound of formula (IV), according to the scheme 4:

The reaction can be carried out as described above for the preparation of compounds of formula (I) wherein W has the meanings other than COOH or —COO—$C_1$-$C_4$-alkyl.

The hydrolysis of the ester group in step b) can be carried out in basic conditions, in the manner known in the art. As the examples of the base, alkaline metal hydroxides can be mentioned, such as sodium, potassium and lithium hydroxides. For preparing single enantiomers of a compound of formula (I), it is preferable to carry out the hydrolysis with lithium hydroxide, which allows for the retention of the configuration.

Basic hydrolysis in step b) can be for example carried out in a three-solvent system consisting of THF (tetrahydrofuran), methanol and water, which allows to obtain homogenous reaction mixture. At the end of the hydrolysis, the reaction mixture can be neutralized with hydrochloric acid and, if desired, the free acid product can be extracted, for example with ethyl acetate, according to the scheme 5 shown below:

Scheme 5

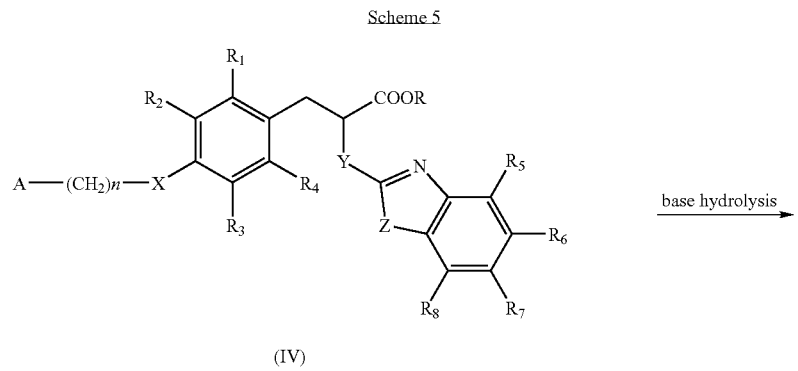

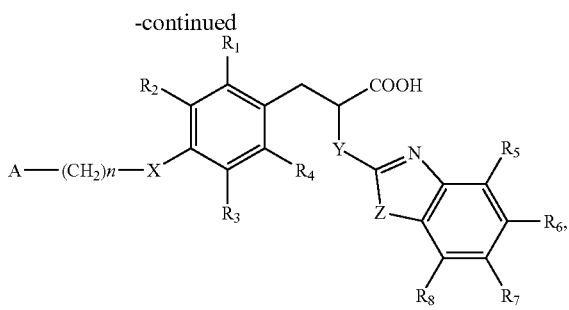

W = COOH (I)

Compounds of formula (I) wherein Y=S, and X, W, Z, A, n, and $R_1$ to $R_8$ have the meanings as defined above, can be prepared by reaction of a compound of formula (V) wherein W, X, A, n, and $R_1$ to $R_4$ have the meanings as defined above for formula (I), with a compound of formula (VI) wherein Z and $R_5$ to $R_8$ have the meanings as defined above for formula (I), in the presence of a base in an alcoholic solution, according to the scheme 6.

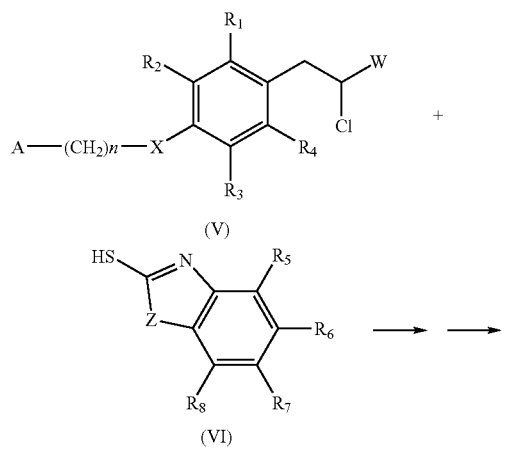

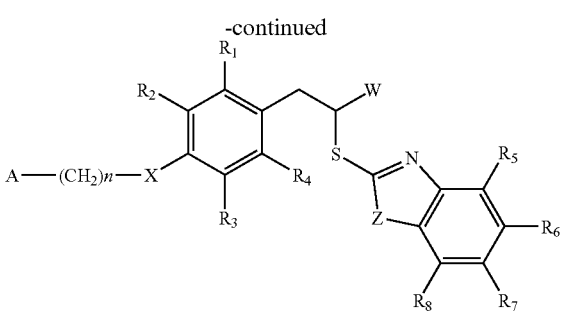

In the case of the preparation of compounds of formula (I) wherein W represents COOH group, the starting compound in the above process is a compound of formula (V) wherein W is an ester-protected COOH group, as illustrated in the scheme 7. At the end of the reaction, COOH group is deprotected by basic hydrolysis.

According to the scheme 7, the first reaction step, giving ethyl 2-chloro-3-phenylpropionate derivatives, is performed according to the method described by Y. Kawamatsu, H. Asakawa, T. Saraie, E. Imamiya, K. Nishikawa, Y. Hamuro, Arzneim.Forsch./Drug Res./, 30 (I), 4, 1980, 585-589. Chloroester obtained in the Meerwein reaction is reacted with 1,3-benzoxazole-2-thiol, in the presence of a base in an alcoholic solution, to give corresponding ethyl α-(1,3-benzoxazol-2-ylthio)ester. This ester is hydrolyzed in the NaOH or KOH aqueous-alcoholic solution. Free acids are released from salts with diluted hydrochloric acid.

Scheme 7

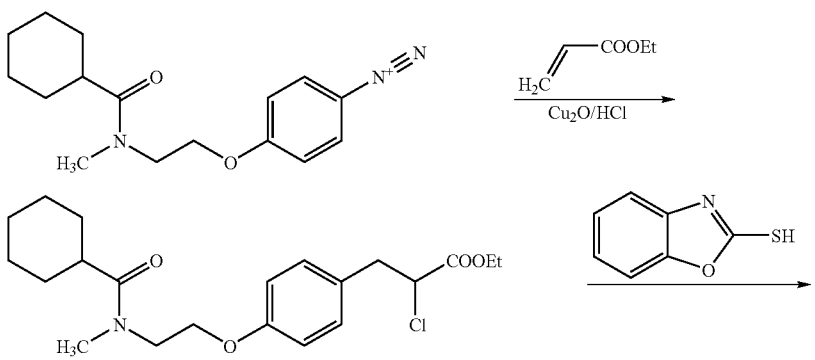

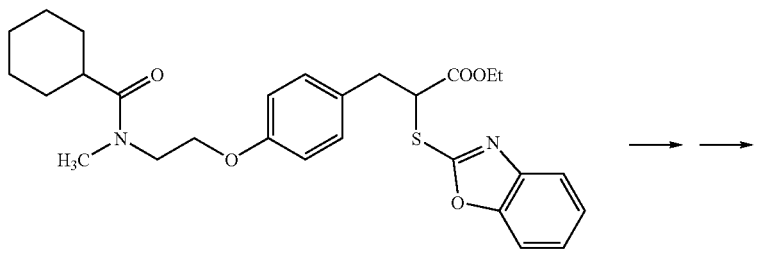

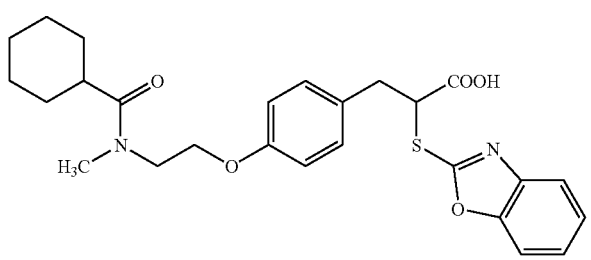

In an analogous manner, the following exemplary compounds were obtained.

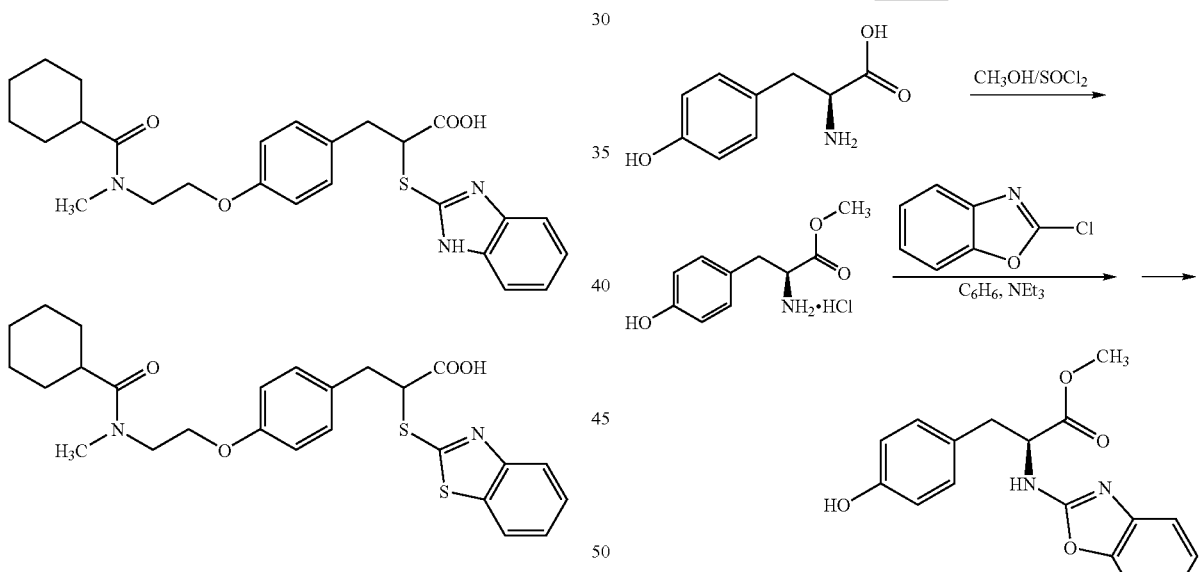

Scheme 8

Compounds of formula (I) can be prepared both in a racemic form and in a form of a single enantiomer, when starting from optically active materials. Alternatively, racemic compounds of formula (I) can be resolved into enantiomers, using conventional techniques known in the art.

Tyrosine derivatives of formula (III) wherein X=O, Y=NH, and Z=O, were obtained according to Shyam B. Advani, Joseph Sam, Journal of Pharmaceutical Sciences, Vol. 57, 10, 1968. For example, according to the scheme 8, L-tyrosine methyl ester hydrochloride was obtained by esterification of L-tyrosine with methanol in the presence of thionyl chloride, followed by the reaction of L-tyrosine methyl ester hydrochloride with 2-chloro-1,3-benzoisoxazole in benzene in the presence of triethylamine. Similar procedures were used in the case of D-tyrosine and D,L-tyrosine.

Tyrosine compounds of formula (III) wherein X=O, Y=NH, and Z=NH, N-alkyl, N-aryl, N-heteroaryl or S, can be prepared by adapting the method of Shyam B. Advani, Joseph Sam, Journal of Pharmaceutical Sciences, Vol. 57, 10, 1968, described above.

Tyrosine derivatives of formula (III) wherein X=O, Y=NH, and Z=S, can be prepared according to the method described in Edward S. Lazer, Clara K. Miao, Hin-Chor Wong, Rondla Sorcek, Denice M. Spero, Alex Galman, Kollol Pal, Mark Behnke, Anne G. Graham, Jane M. Watrous, Carol A. Homon, Juergen Nagle, Arvind Shah, Yvan Guindon, Peter R. Farina, Julian Adams, J. Med. Chem., 1994, 37, 913-923, according to the scheme 9.

Scheme 9

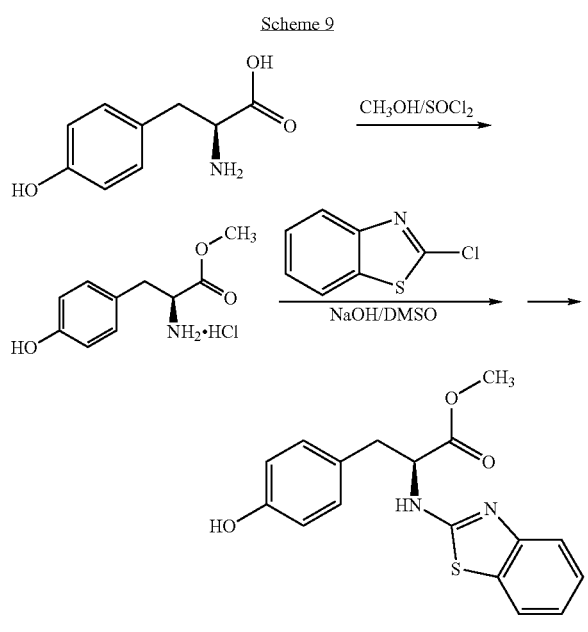

4-Mercaptophenylalanine derivatives of formula (III) wherein Y=NH, Z=O, and X=S, were prepared according to the scheme 10, from 4-mercaptophenylalanine, which was obtained according to Helen S. M. Lu, Martin Volk, Yuriy Kholodenko, Edward Gooding, Robin M. Hochstrasser, William F. DeGrado, Journal of the American Chemical Society, 119,31,1997,7173-7180. The mercapto (SH) group in 4-mercaptophenylalanine was protected with trityl group, followed by substitution of one hydrogen atom at α-amino nitrogen atom with 2-benzoxazolyl. The final step of the synthesis is deprotection of the SH group.

Scheme 10

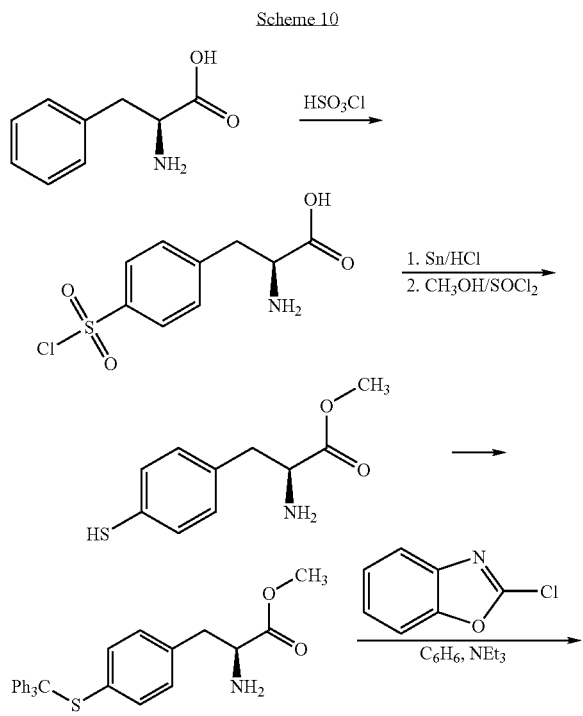

The 4-aminophenylalanine derivatives of formula (III) wherein Y=NH, Z=O, and X=NSO$_2$—CH$_3$, were obtained according to the scheme 11 from 4-nitro-N-phthaloylphenylalanine methyl ester. The first step of the synthesis was performed according to F. Bergel, J. A. Stock, Journal of Organic Chemistry, 1956, 90-96. 4-Amino-N-phthaloylphenylalanine methyl ester thus obtained was mesylated with mesyl chloride in pyridine in the presence of catalytic amounts of DMAP. The subsequent step was the removal of phthaloyl group, by heating with 6M aqueous HCl. Thus obtained 4-methanesulfonyl-aminophenylalanine was converted into methyl ester hydrochloride by esterification in methanol in the presence of thionyl chloride. The subsequent step was the reaction of 4-methanesulfonylaminophenylalanine methyl ester hydrochloride with 2-chlorobenzoxazole in the presence of triethylamine in benzene.

Scheme 11

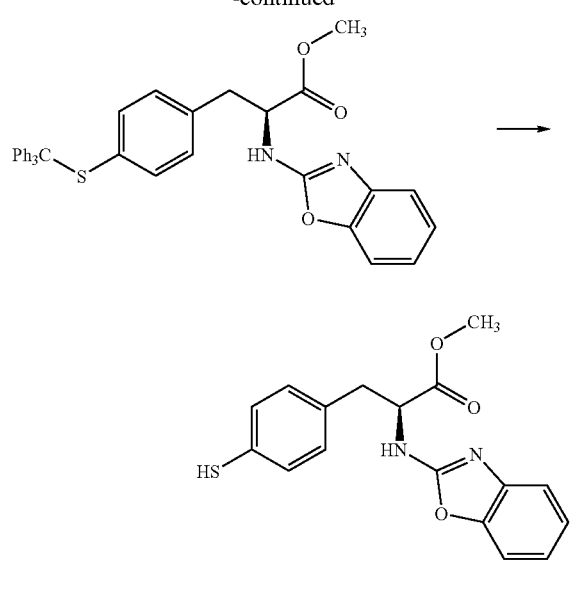

-continued

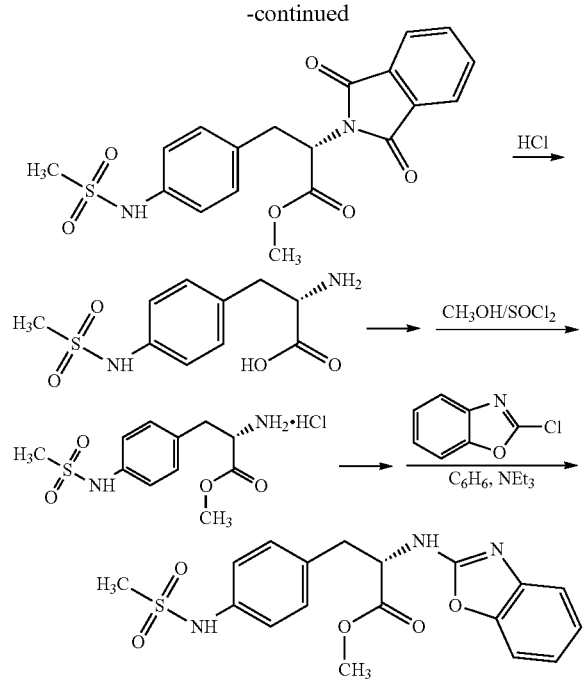

Starting compounds of formula (VI) wherein Z=O, i.e. substituted 2-mercaptobenzoxazoles can be obtained according to Roger Lok, Rondla E. Leone, Antony J. Williams, J. Org. Chem., 61, 3289-3297, in the reaction of a compound of formula (VII) wherein $R_5$ to $R_8$ have the meanings as defined for formula (I) above, as illustrated on the scheme 12.

Scheme 12

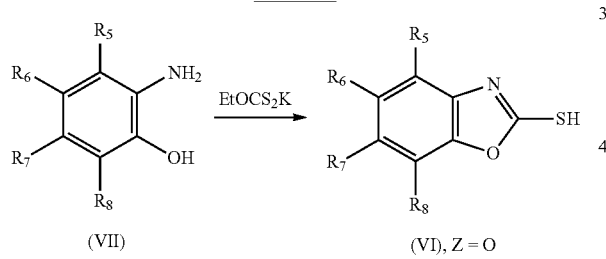

Starting compounds of formula (VIII), i.e. substituted 2-chloro-benzoxazoles can be obtained by using or adapting procedures described in Fortuna Haviv, James D. Ratajczyk, Robert W. DeNet, Francis A. Kerdesky, Rolad L. Walters, Steven P. Schmidt, James H. Holmes, Patrick R. Young, George W. Carter, J. Med. Chem., 1988, 31, 1719-1728, by reaction of a compound of formula (VI) wherein $R_5$ to $R_8$ have the meanings as defined for formula (I) above, with phosphorus pentoxide, according to the scheme 13.

Scheme 13

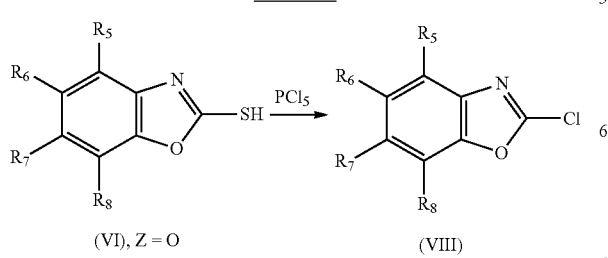

3-[4-(Benzyloxy)phenyl]-2-hydroxypropionic acid ethyl ester was obtained according to Takamura Makoto, Yanagisawa Hiroaki, Kanai Motoru, Shibasaki Masakatsu, Efficient Synthesis of Antihyperglycemic (S)-α-Aryloxy-β-phenyl-propionic Amides Using a Bifunctional Asymmetric Catalyst, *Chem. Pharm. Bull.*, 50, 8, 2002,1118-1121. Subsequently, the ester was treated with sodium hydride and then with 2-chlorobenzoxazole, according to the scheme 14.

Scheme 14

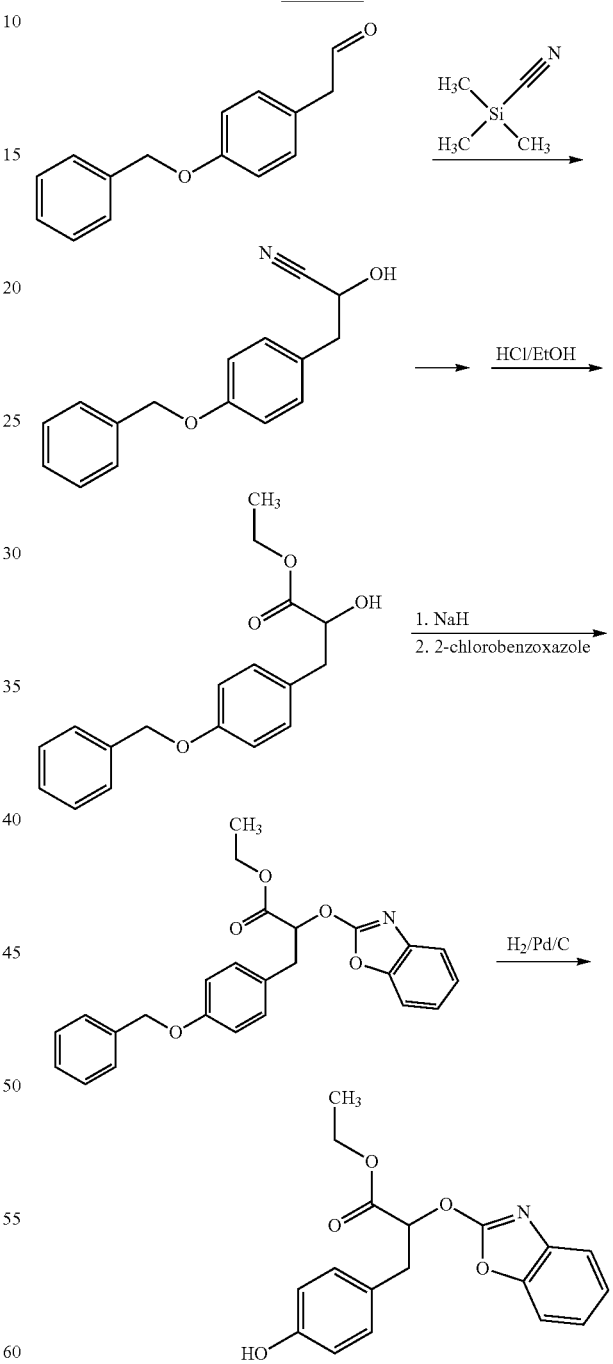

The following abbreviations are used herein:
DIAD: diisopropyl azodicarboxylate
DEAD: diethyl azodicarboxylate
ADDP: azodicarbonyldipiperidine

EXAMPLES

Example 1

(2S)-2-(1,3-Benzoxazol-2-ylamino)-3-[4-(2,3-dihydro-1,4-benzodioxin-6-yl-methoxy)phenyl]propionic acid and its methyl ester $R_1$ to $R_8$=H, W=COOH/COOCH$_3$, X=O, Z=O, Y=NH, n=1, A=2,3-dihydro-1,4-benzodioxin-6-yl of the formula:

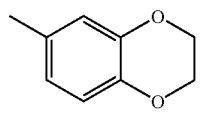

2,3-Dihydro-1,4-benzodioxin-6-ylmethanol (0.25 g, 1.5 mmol), methyl (2S)-2-(1,3-benzoxazol-2-ylamino)-3-(4-hydroxyphenyl)propionate (0.31 g, 1 mmol) and triphenylphosphine (0.26 g, 1 mmol) were dissolved in 5 ml of tetrahydrofuran (THF). The reaction mixture was cooled to 5° C. DIAD (0.61 g, 3 mmol) was then added and the reaction was stirred at room temperature for 18-24h. Subsequently, THF was evaporated to obtain the product, the title acid methyl ester.

The crude product was dissolved in a THF/MeOH/H$_2$O mixture (6:0.1:1, 2 ml). 1M LiOH (1.6 ml) was added and the reaction was stirred for 3 days at room temperature. Then the reaction mixture was neutralized with 1M HCl, a small amount of water was added and the mixture was extracted with ethyl acetate. The solvent was evaporated. The purification was performed by chromatography. The yield was 50%. MS (ES) 446 (M$^+$, 100%)

Example 2

(2S)-2-(1,3-Benzoxazol-2-ylamino)-3-[4-((3,5-dimethylisoxazol-4-yl)methoxy)-phenyl]propionic acid and its methyl ester $R_1$ to $R_8$=H, W=COOH/COOCH$_3$, Y=NH, X=O, Z=O, n=1, A=3,5-dimethylisoxazol-4-yl of the formula:

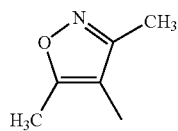

(3,5-Dimethylisoxazol-4-yl)methanol (0.28 g, 1.5 mmol), methyl (2S)-2-(1,3-benzoxazol-2-ylamino)-3-(4-hydroxyphenyl)propionate (0.31 g, 1 mmol) and triphenylphosphine (0.26 g, 1 mmol) were dissolved in 5 ml of tetrahydrofuran (THF). The reaction mixture was cooled to 5° C. DEAD (0.52 g, 3 mmol) was then added and the reaction was stirred at room temperature for 18-24 h. Subsequently, THF was evaporated to obtain the product, the title acid methyl ester.

The crude product was dissolved in a THF/MeOH/H$_2$O mixture (6:0.1:1, 2 ml). 1M LiOH (1.6 ml) was added and the reaction was stirred for 3 days at room temperature. Then the reaction mixture was neutralized with 1M HCl, a small amount of water was added and the mixture extracted with ethyl acetate. The solvent was evaporated. The purification was performed by chromatography. The yield was 60%. MS (ES) 407 (M$^+$, 100%)

Example 3

(2S)-2-(1,3-Benzoxazol-2-ylamino)-3-[4-(2-[(cyclohexylcarbonyl)(methyl)-amino]ethoxy)phenyl]propionic acid and its methyl ester $R_1$ to $R_8$=H, W=COOH/COOCH$_3$, X=O, Z=O, Y=NH, n=2, A=(cyclohexyl-carbonyl)methylamino group of the formula:

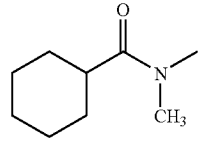

N-(2-Hydroxyethyl)-N-methylocyclohexanecarboxyamide (0.19 g, 1.5 mmol), methyl (2S)-2-(1,3-benzoxazol-2-ylamino)-3-(4-hydroxyphenyl)-propionate (0.31 g, 1 mmol) and triphenylphosphine (0.26 g, 1 mmol) were dissolved in 5 ml of tetrahydrofuran (THF). The reaction mixture was cooled to 5° C. ADDP (0.76 g, 3 mmol) was then added and the reaction was stirred at room temperature for 18-24 h. Subsequently, THF was evaporated to obtain the product, the title acid methyl ester.

The crude product was dissolved in a THF/MeOH/H$_2$O mixture (6:0.1:1; 2 ml). Aqueous 1M LiOH solution (1.6 ml) was added and the reaction was stirred for 3 days at room temperature. Then the reaction mixture was neutralized with 1M HCl, a small amount of water was added and the mixture extracted with ethyl acetate. The solvent was evaporated. The purification was performed by chromatography. The yield was 40%. MS (ES) 465 (M$^+$, 100%)

Example 4

(2S)-2-(1,3-Benzoxazol-2-ylamino)-3-[4-(2-[5-methyl-2-(3,4,5-trimethoxy-phenyl)-1,3-oxazol-4-yl]ethoxy)phenyl]propionic acid and its methyl ester $R_1$ to $R_8$=H, W=COOH/COOCH$_3$, X=O, Z=O, Y=NH, n=2, A=[5-methyl-2-(3,4,5-trimethoxyphenyl)-1,3-oxazol-4-yl] of the formula:

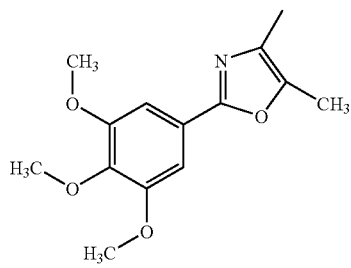

To the solution of 2-[4-methyl-2-(3,4,5-trimethoxyphenyl)-1,3-oxazol-5-yl]ethanol (2.93 g, 10 mmol) in 30 ml of pyridine 4-toluenesulfonyl chloride (1.9 g, 10 mmol) was added portionwise at room temperature. Subsequently, the reaction mixture was stirred for 5 h at room temperature, and then poured into 200 ml of water and extracted (3×) with 50 ml of dichloromethane. The combined extracts were washed with 1M HCl, an aqueous solution of sodium bicarbonate, and brine. The organic phase was dried over magnesium sulfate and the solvent was evaporated, to obtain a product, 2-[4-methyl-2-(3,4,5-trimethoxyphenyl)-1,3-oxazol-5-yl] ethyl 4-toluenesulfonate having the purity of ca. 95%.

To the solution of 3.12 g of methyl (2S)-2-(1,3-benzoxazol-2-ylamino)-3-(4-hydroxyphenyl)propionate in 50 ml of dimethylformamide 60% suspension of NaH in mineral oil (0.4 g) was added portionwise with stirring at room temperature under argon atmosphere. When the evolution of the gas ceased, the solution of 2-[4-methyl-2-(3,4,5-trimethoxyphenyl)-1,3-oxazol-5-yl]ethyl 4-toluenesulfonate (4.47 g, 10 mmol) in dimethylformamide was added dropwise. The mixture was heated at 80° C. with stirring. After cooling, the mixture was poured into 1 l of water and extracted several times with ethyl acetate. The combined extracts were washed with brine, dried over magnesium sulfate and the solvent was evaporated, to obtain crude methyl (2S)-2-(1,3-benzoxazol-2-ylamino)-3-[4-(2-[5-methyl-2-(3,4,5-trimethoxy-phenyl)-1,3-oxazol-4-yl]ethoxy)phenyl]propionate.

2.9 g of the crude reaction product obtained above were dissolved in a THF/MeOH/H$_2$O mixture (6:0.1:1, 20 ml). 1M LiOH (8 ml) was added and the reaction mixture was stirred for 3 days at room temperature. Then the reaction mixture was neutralized with 1M HCl, a small amount of water was added and the mixture extracted with ethyl acetate. The solvent was evaporated. The purification was performed by chromatography. The yield was 40%. MS (ES) 573 (M$^+$, 100%)

Example 5

(2S)-2-(1,3-Benzoxazol-2-ylamino)-3-[4-(4-{2-[[6-(2-chlorophenyl)-5-cyano-2-(methylthio)pyrimidin-4-yl](methyl)amino]ethoxy})phenyl]propionic acid and its methyl ester $R_1$ to $R_8$=H, W=COOH/COOCH$_3$, X=O, Z=O, Y=NH, n=2, A=[6-(2-chlorophenyl)-5-cyano-2-(methylthio)pyrimidin-4-yl](methyl)amino group of the formula:

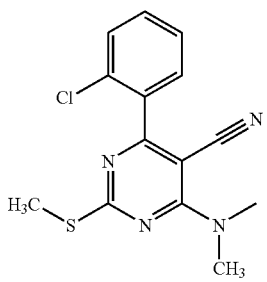

4-(2-Chlorophenyl)-6-[(2-hydroxyethyl)(methyl)amino]-2-(methylthio)-pyrimidine-5-carbonitrile (0.50 g, 1.5 mmol), methyl (2S)-2-(1,3-benzoxazol-2-ylamino)-3-(4-hydroxyphenyl)propionate (0.31 g, 1 mmol) and triphenyl-phosphine (0.26 g, 1 mmol) were dissolved in 5 ml of tetrahydrofuran (THF). The reaction mixture was cooled to 5° C. DEAD (0.52 g, 3 mmol) was then added and the reaction was stirred at room temperature for 18-24 h. Subsequently, THF was evaporated to obtain the product, the title acid methyl ester.

The crude product was dissolved in a THF/MeOH/H$_2$O mixture (6:0,1:1, 2 ml). 1M LiOH (1.6 ml) was added and the reaction was stirred at room temperature for 3 days. Then the reaction mixture was neutralized with 1M HCl, a small amount of water was added and the mixture extracted with ethyl acetate. The solvent was evaporated. The purification was performed by chromatography. The yield was 58%. MS (ES) 614 (M$^+$, 100%)

Example 6

(2S)-2-(1,3-Benzoxazol-2-ylamino)-3-[4-(2-(2-tert-butyl-5-methyl-1,3-oxazol-4-yl)ethoxy)phenyl]propionic acid and its methyl ester $R_1$ to $R_8$=H, W=COOH/COOCH$_3$, X=O, Z=O, Y=NH, n=2, A=2-tert-butyl-5-methyl-1,3-oxazol-4-yl of the formula:

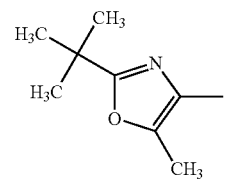

2-(2-tert-Butyl-4-methyl-1,3-oxazol-5-yl)ethanol (0.27 g, 1,5 mmol), methyl (2S)-2-(1,3-benzoxazol-2-ylamino)-3-(4-hydroxyphenyl)propionate (0.31 g, 1 mmol) and triphenylphosphine (0.26 g, 1 mmol) were dissolved in 5 ml of tetrahydrofuran (THF). The reaction mixture was cooled to 5° C. DEAD (0.52 g, 3 mmol) was then added and the reaction was stirred at room temperature for 18-24 h. Subsequently, THF was evaporated to obtain the product, the title acid methyl ester.

The crude product was dissolved in a THF/MeOH/H$_2$O mixture (6:0.1:1, 2 ml). 1M LiOH (1.6 ml) was added and the reaction was stirred at room temperature for 3 days. Then the reaction mixture was neutralized with 1M HCl, a small amount of water was added and the mixture extracted with ethyl acetate. The solvent was evaporated. The purification was performed by chromatography. The yield was 55%. MS (ES) 463 (M$^+$, 100%)

Example 7

(2S)-2-(1,3-Benzoxazol-2-ylamino)-3-[4-(2-[(cyclohexylcarbonyl)(methyl)-amino]thioethoxy)phenyl] propionic acid and its methyl ester $R_1$ to $R_8$=H. W=COOH/COOCH$_3$, X=S, Z=O, Y=NH, n=2, A=(cyclohexylcarbonyl)(methyl)amino group of the formula:

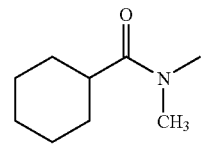

N-(2-Hydroxyethyl)-N-methylcyclohexanecarboxyamide (0.19 g, 1.5 mmol), methyl (2S)-2-(1,3-benzoxazol-2-ylamino)-3-(4-mercaptophenyl)-propionate (0.33 g, 1 mmol) and triphenylphosphine (0.26 g, 1 mmol) were dissolved in 5 ml of tetrahydrofuran (THF). The reaction mixture was cooled to 5° C. DEAD (0.52 g, 3 mmol) was then added and the reaction was stirred at room temperature for 18-24 h. Subsequently, THF was evaporated to obtain the product, the title acid methyl ester.

The crude product was dissolved in a THF/MeOH/H$_2$O mixture (6:0.1:1, 2 ml). 1M LiOH (1.6 ml) was added and the reaction was stirred at room temperature for 3 days. Then the reaction mixture was neutralized with 1M HCl, a small amount of water was added and the mixture extracted with ethyl acetate. The solvent was evaporated. The purification was performed by chromatography. The yield was 46%. MS (ES) 481 (M$^+$, 100%)

Example 8

(2S)-2-(1,3-benzoxazol-2-ylamino)-3-[4-(2-[(cyclohexylcarbonyl)(methyl)-amino]ethylmetanesulfonylamino)phenyl]propionic acid and its methyl ester R$_1$ to R$_8$=H, W=COOH/COOCH$_3$, X=CH$_3$SO$_2$N, Z=O, Y=NH, n 2, A=(cyclohexylcarbonyl)(methyl)amino group of the formula:

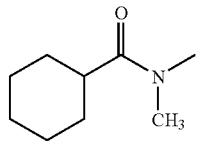

N-(2-hydroxyethyl)-N-methylcyclohexanecarboxyamide (0.19 g, 1.5 mmol), methyl (2S)-2-(1,3-benzoxazol-2-ylamino)-3-(4-methanesulfonylamino-phenyl)propionate (0.39 g, 1 mmol) and triphenylphosphine (0.26 g, 1 mmol) were dissolved in 5 ml of tetrahydrofuran (THF). The reaction mixture was cooled to 5° C. DEAD (0.52 g, 3 mmol) was then added and the reaction was stirred at room temperature for 18-24 h. Subsequently, THF was evaporated to obtain the product, the title acid methyl ester.

The crude product was dissolved in a THF/MeOH/H$_2$O mixture (6:0.1:1, 2 ml). 1M LiOH (1.6 ml) was added and the reaction was stirred at room temperature for 3 days. Then the reaction mixture was neutralized with 1M HCl, a small amount of water was added and the mixture extracted with ethyl acetate. The solvent was evaporated. The purification was performed by chromatography. The yield was 35%. MS (ES) 542 (M$^+$, 100%)

Example 9

(2S)-2-(1,3-Benzothiazol-2-ylamino)-3-[4-(2-[(cyclohexylcarbonyl)(methyl)-amino]ethoxy)phenyl]propionic acid and its methyl ester R$_1$ to R$_8$=H, W=COOH/COOCH$_3$, X=O, Z=S, Y=NH, n=2, A=(cyclohexylcarbonyl)(methyl)amino group of the formula:

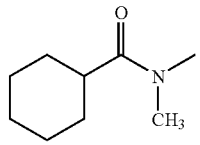

N-(2-hydroxyethyl)-N-methylcyclohexanecarboxyamide (0.19 g, 1.5 mmol), methyl (2S)-2-(1,3-benzothiazol-2-ylamino)-3-(4-hydroxyphenyl)-propionate (0.33 g, 1 mmol) and triphenylphosphine (0.26 g, 1 mmol) were dissolved in 5 ml of tetrahydrofuran (THF). The reaction mixture was cooled to 5° C. DEAD (0.52 g, 3 mmol) was then added and the reaction was stirred at room temperature for 18-24 h. Subsequently, THF was evaporated to obtain the product, the title acid methyl ester.

The crude product was dissolved in a THF/MeOH/H$_2$O mixture (6:0.1:1, 2 ml). 1M LiOH (1.6 ml) was added and the reaction was stirred at room temperature for 3 days. Then the reaction mixture was neutralized with 1M HCl, a small amount of water was added and the mixture extracted with ethyl acetate. The solvent was evaporated. The purification was performed by chromatography. The yield was 48%. MS (ES) 481 (M$^+$, 100%)

Example 10

(2S)-2-(1,3-benzoxazol-2-yloxy)-3-[4-(2-[(cyclohexylcarbonyl)(methyl)-amino]ethoxy)phenyl]propionic acid and its methyl ester R$_1$ to R$_8$=H, W=COOH/COOCH$_3$, X=O, Z=O, Y=O, n=2 A=(cyclohexylcarbonyl)methylaminoethyl of the formula

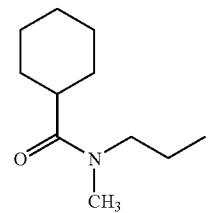

N-(2-Hydroxyethyl)-N-methylcyclohexanecarboxyamide (0.19 g, 1.5 mmol), ethyl 2-(1,3-benzoxazol-2-yloxy)-3-(4-hydroxyphenyl)propionate (0.33 g, 1 mmol) and triphenylphosphine (0.26 g, 1 mmol) were dissolved in 5 ml of tetrahydrofuran (THF). The reaction mixture was cooled to 5° C. DEAD (0.52 g, 3 mmol) was then added and the reaction was stirred at room temperature for 18-24 h. Subsequently, THF was evaporated to obtain the product, the title acid methyl ester.

The crude product was dissolved in a THF/MeOH/H$_2$O mixture (6:0.1:1, 2 ml). 1M LiOH (1.6 ml) was added and the mixture was at room temperature for 3 days. Then the reaction mixture was neutralized with 1M HCl, a small amount of water was added and the mixture extracted with ethyl acetate. The solvent was evaporated. The purification was performed by chromatography. The yield was 40%. MS (ES) 466 (M$^+$, 100%)

Biological Tests

The ability of the compounds of the invention to bind to the PPAR gamma receptor and to modify its activity was determined using the following methods.

In vitro Binding

The ability of the compounds to bind to the PPAR gamma receptor (in vitro) was determined according to the procedure described below, using the method of competitive radioligand displacement from the ligand-receptor complex. PPAR agonist $^3$H-rosiglitazone at final concentration 10 nM was used as the radioligand. An excess of unlabelled test compounds at final concentration 20 μM was also added to the reaction. The source of the receptor in assays was human recombinant protein containing LBD (ligand binding domain) of the PPAR gamma. The separation of the radioligand unbound with the receptor was performed by dextran coated charcoal technique. The radioactivity was measured using LS 6500-Beckman Coulter scintillation counter. The obtained scintillation counts values were compared to the values obtained for samples incubated with the radioligand (assumed 0% displacement) and to the values obtained for samples containing both the radioligand and an excess of non-radiolabelled rosiglitazone (assumed 100% displacement). The obtained values were comprised in the 0-130% range.

References:
1. ADD1/SREBP1 activates PPAR gamma through the production of endogenous Ligand. Proc. Natl. Acad. Sci. U S A. 1998 Apr. 14;95(8):4333-7.
2. An antidiabetic thiazolidinedione is a high affinity Ligand for peroxisome proliferator-activated receptor gamma (PPAR gamma). J. Biol. Chem. 1995 Jun. 2;270(22):12953-6.
3. Fatty acids and eicosanoids regulate gene expression through direct interactions with peroxisome proliferator-activated receptors alpha and gamma. Proc. Natl. Acad. Sci. U S A. 1997 Apr. 29; 94(9):4318-23.

Binding in Adipocytes

To confirm the ability of the tested molecules to bind in vivo, analogous experiments with the use of murine fibroblasts 3T3-L1 cell line differentiated into adipocytes were performed. Differentiation of fibroblasts cells was performed on 12-well plates during 10 days period. On the day of the experiment, the cells were washed twice with PBS solution prior to 1 h incubation in DMEM medium containing tritium-labelled reference compound (rosiglitazone) at 30 pM concentration) and different concentrations of the tested compounds (in the 100 pM -20 µM concentration range) at 37° C. Then the cells were washed three times with PBS solution and solubilized in 1M NaOH solution. In the lysate prepared as described above, both radioactivity (using LS 6500 Beckman Coulter scintillation counter) and protein concentration (using Bradford method) were measured. Nonspecific binding was estimated in the presence of non-labelled reference compound (at 20 µM concentration).

The obtained scintillation counts values were compared to the values obtained for samples incubated with the radioligand (assumed 0% displacement) and to the values obtained for samples containing both the radioligand and an excess of non-radiolabelled rosiglitazone (assumed 100% displacement). The obtained values were comprised in the 0-130% range.

References:
1. Identification of high-affinity binding sites for the insulin sensitizer rosiglitazone (BRL-49653) in rodent and human adipocytes using a radioiodinated ligand for peroxisomal proliferator-activated receptor gamma. J. Pharmacol. Exp. Ther. 1998 Febuary;284(2):751-9.
2. Differential regulation of the stearoyl-CoA desaturase genes by thiazolidinediones in 3T3-L1 adipocytes. J. Lipid Res. 2000 August;.41(8):1310-6.
3. Distinct stages in adipogenesis revealed by retinoid inhibition of differentiation after induction of PPARgamma. Mol Cell Biol. 1996 Apr.;16(4):1567-75.
4. Differentiation Kinetics of in vitro 3T3-L1 Preadipocyte Cultures. Tissue Eng. 2002 Dec.;8(6):1071-1081.
5. Role of PPARgamma in regulating a cascade expression of cyclin-dependent kinase inhibitors, p18(INK4c) and p21(Waf1/Cip1), during adipogenesis. J. Biol. Chem. 1999 Jun. 11 ;274(24): 17088-97.

Adipogenesis

3T3-L1 cell line cells (from ATCC) were maintained in Dulbecco's Modified Eagle's Medium supplemented with 10% Fetal Bovine Serum and antibiotics. Two days before the experiment, the cells were passaged into 12-well microplates ($30 \times 10^4$ cells/well) and maintained for subsequent 2 days to confluency. After this time, the medium was replaced with DMEM+FBS+antibiotics and tested compounds at final concentration of 50 µM were added to the cells. Under these conditions, the cells were maintained for 14 days, changing the medium with the test compounds every 2 days. After 10-14 days the differentiated cells were stained with Oil Red O prior to photographing.

References:
1. Differential regulation of the stearoyl-CoA desaturase genes by thiazolidinediones in 3T3-L1 adipocytes. J. Lipid Res. 2000 August;41(8):1310-6.

Glucose Uptake

Differentiated 3T3-L1 fibroblasts were incubated in DMEM supplemented with 10% FBS and antibiotics with test compounds (at the concentration of 20 µM) for 48 h. After this time, the cells were washed with PBS, and then serum-free DMEM was added to the cells. The cells were kept in an incubator for 3 h (37° C./5% $CO_2$) and then medium was replaced with KHR buffer (25 mM HEPES-NaOH; pH 7.4; 125 mM NaCl; 5 mM KCl; 1.2 mM $MgSO_4$; 1.3 mM $CaCl_2$; 1.3 mM $KH_2PO_4$) and the cells were incubated for 30 minutes at 37° C. Glucose uptake was initiated by the addition to each test well of 50 µl KRH buffer containing 0.5 mM 2 deoxy-D-[1,2-$^3$H]glucose (0.5 µCi) and 100 nM insulin. After 10 min incubation at 37° C., the medium was aspirated, and the cells were washed three times with ice-cold KRH buffer. Then the cells were dissolved in 1M NaOH. In the lysate prepared as described above, both radioactivity (using LS 6500 Beckman Coulter scintillation counter) and protein concentration (using Bradford method) were measured. Nonspecific binding was estimated in the presence of non-labelled reference compound (at 20 µM concentration).

REFERENCE

1. Role of peroxisome proliferator-activated receptor-gamma in maintenance of the characteristics of mature 3T3-L1 adipocytes. Diabetes. 2002 July;51 (7):2045-55.
2. Identification of high-affinity binding sites for the insulin sensitizer rosiglitazone (BRL-49653) in rodent and human adipocytes using a radioiodinated ligand for peroxisomal proliferator-activated receptor gamma. J. Pharmacol. Exp. Ther. 1998 Febuary; 284(2):751-9.
3. Identification of bioactive molecules by adipogenesis profiling of organic compounds. J. Biol. Chem. 2003 Feb. 28;278(9):7320-4. Epub 2002 Dec 19.
4. Evidence for the involvement of vicinal sulfhydryl groups in insulin-activated hexose transport by 3T3-L1 adipocytes. J. Biol. Chem. 1985 Mar. 10;260(5):2646-52.

The invention claimed is:

1. A method of treatment of diseases and conditions mediated by peroxysome proliferator-activated receptor gamma (PPARγ) wherein said disease or condition is selected from the group consisting of hypertension, obesity, hyperglycemia and atherosclerosis; insulin resistance; type 2 diabetes; peripheral neuropathy, renal insufficiency, and retinopathy, in a mammal subject in need thereof, said method comprising administration to said mammal a compound of formula (I):

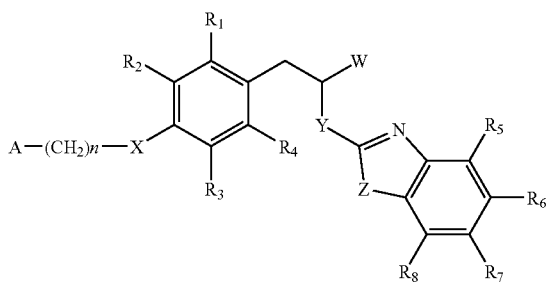

(I)

wherein:
W represents COOH group or —COO—$C_1$-$C_4$-alkyl group;
Y represents NH, N—$C_1$-$C_{10}$-alkyl, O, or S;
Z represents O;
X represents O, S, NH, N—$C_1$-$C_{10}$-alkyl, N-aryl, NSO$_2$—$C_1$-$C_{10}$-alkyl, N—SO$_2$-aryl, or N—SO$_2$-heteroaryl;
$R_1$ to $R_8$ each independently represent hydrogen atom or a substituent selected from the group consisting of:
$C_1$-$C_4$-alkyl, $C_1$-$C_4$-alkoxy, $C_3$-$C_7$-cycloalkyl, $C_3$-$C_7$-cycloalkoxy, $C_1$-$C_4$-thioalkoxy, $C_3$-$C_7$-cyclothioalkoxy, halogen atom, halogen-substituted $C_3$-$C_7$-cycloalkyl, aryl, heteroaryl, —NO$_2$, —CN, —SO$_2$—NH$_2$, —SO$_2$—NH—$C_1$-$C_4$-alkyl, —SO$_2$—N($C_1$-$C_4$-alkyl)$_2$, —CO—$C_1$-$C_4$-alkyl, —O—CO—$C_1$-$C_4$-alkyl, —CO—O—$C_1$-$C_4$-alkyl, —CO-aryl, —CO—NH$_2$, —CO—NH—$C_1$-$C_4$-alkyl, and —CO—N($C_1$-$C_4$-alkyl)$_2$;
A represents $C_3$-$C_7$-cycloalkyl, halogen-substituted $C_3$-$C_7$-cycloalkyl, aryl, heteroaryl selected from the group consisting of pyrrol-1-yl, pyrrol-2-yl, pyrrol-3-yl, furyl, thienyl, imidazolyl, oxazolyl, thiazolyl, isoxazolyl, 1,2,4-triazolyl, oxadiazolyl, thiadiazolyl, tetrazolyl, pyridinyl, pyrimidinyl, 1,3,5-triazinyl, indolyl, benzo[b]furyl, benzo[b]thienyl, indazolyl, benzimidazolyl, azaindolyl, cynnolyl, isoquinolinyl, and carbazolyl; heterocyclyl, —NH—CO—$C_1$-$C_4$-alkyl, —N($C_1$-$C_4$-alkyl)—CO—$C_1$-$C_4$-alkyl, —NH—CO-aryl, —N($C_1$-$C_4$-alkyl)—CO-aryl, —N($C_1$-$C_4$-alkyl)—CO—$C_3$-$C_7$-cycloalkyl, —NH—CO—NH$_2$, —NH—CO—NH—$C_1$-$C_4$-alkyl, —NH—CS—NH—$C_1$-$C_4$-alkyl, —NH—CO—NH-aryl, —NH—CS—NH-aryl, —N($C_1$-$C_4$-alkyl)—CO-heteroaryl, —SO$_2$—$C_1$-$C_4$-alkyl, —SO$_2$-aryl, or —SO$_2$-heteroaryl; wherein said aryl, heteroaryl and heterocyclyl are optionally substituted with one or more substituents independently selected from the group consisting of $C_1$-$C_4$-alkyl, $C_1$-$C_4$-alkoxy, $C_1$-$C_4$-thioalkoxy, ethylenedioxy, CN, halogen and phenyl, said phenyl being optionally substituted with one or more substituents independently selected from $C_1$-$C_4$-alkyl, $C_1$-$C_4$-alkoxy and halogen atom; and
n represents an integer from 0 to 4, inclusive;
enantiomers thereof and pharmaceutically acceptable salts thereof in a therapeutically effective amount.

2. The method of claim 1 wherein W represents COOH.
3. The method of claim 1 wherein Y represents NH.
4. The method of claim 1 wherein Y represents O.
5. The method of claim 1 wherein Y represents N—$C_1$-$C_4$-alkyl, especially.
6. The method of claim 1 wherein X represents O.
7. The method of claim 1 wherein X represents S.
8. The method of claim 1 wherein X represents NSO$_2$—$C_1$-$C_4$-alkyl, especially.
9. The method of claim 1 wherein W represents COOH, Y represents NH, Z represents O, and X represents O.
10. The method of claim 1 wherein W represents COOH, Y represents O, Z represents O, and X represents O.
11. The method of claim 1 wherein W represents COOH, Y represents NH, Z represents O, and X represents NSO$_2$—$C_1$-$C_4$-alkyl, especially.
12. The method of claim 1 wherein each of $R_1$ to $R_8$ represents hydrogen atom.
13. The method of claim 1 wherein n is equal to 1 or 2.
14. The method of claim 1 wherein A represents heterocyclyl, said heterocyclyl being optionally substituted with one or more substituents independently selected from the group consisting of $C_1$-$C_4$-alkyl, $C_1$-$C_4$-alkoxy, $C_1$-$C_4$-thioalkoxy, CN, halogen atom, and phenyl.
15. The method of claim 1 wherein A represents isoxazolyl, optionally substituted with one or more substituents independently selected from $C_1$-$C_4$-alkyl, especially —CH$_3$.
16. The method of claim 1 wherein A represents phenyl, said phenyl being optionally substituted with ethylenedioxy group.
17. The method of claim 1 wherein A represents N($C_1$-$C_4$-alkyl)—CO—$C_3$-$C_7$ cycloalkyl.
18. The method of claim 17 wherein A represents N(CH$_3$)—CO—cyclohexyl.
19. The method of claim 1 wherein A represents N($C_1$-$C_4$-alkyl)—CO-heteroaryl, said heteroaryl being optionally substituted with one or more substituents independently selected from the group consisting of $C_1$-$C_4$-alkyl, $C_1$-$C_4$-alkoxy, $C_1$-$C_4$-thioalkoxy, CN, halogen atom or phenyl, said phenyl being optionally substituted with one or more substituents independently selected from $C_1$-$C_4$-alkyl, $C_1$-$C_4$-alkoxy, and halogen.
20. The method of claim 19 wherein heteroaryl is pyrimidinyl, optionally substituted with one or more substituents independently selected from the group consisting of $C_1$-$C_4$-alkyl, $C_1$-$C_4$-alkoxy, halogen atom, and phenyl, said phenyl being optionally substituted with one or more substituents independently selected from $C_1$-$C_4$-alkyl, $C_1$-$C_4$-alkoxy, and halogen atom.
21. The method of claim 1, wherein the compound of formula (I) has the stereochemical configuration as shown in formula (IA):

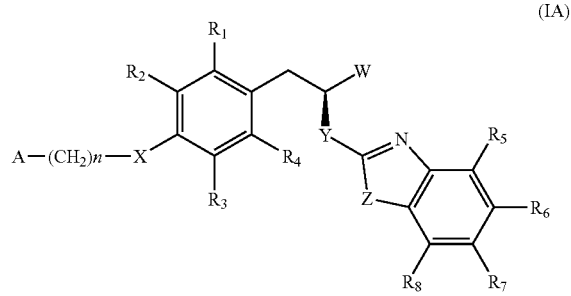

(IA)

and pharmaceutically acceptable salts thereof

22. The method of claim 1, wherein the compound of formula (I) has the stereochemical configuration as shown in formula (IB):

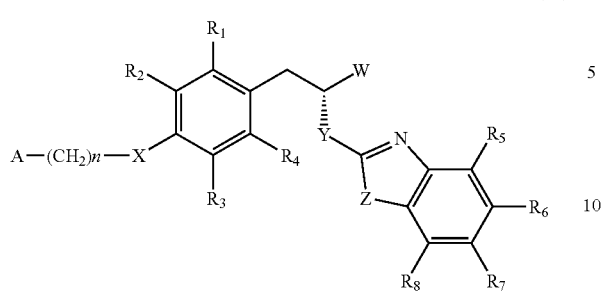

(IB)

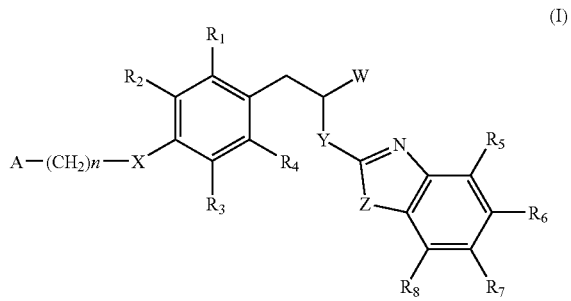

(I)

and pharmaceutically acceptable salts thereof

23. The method of claim 1, wherein the compound of formula (I) is selected from the following:
- (2S)-2-(1,3-benzoxazol-2-ylamino)-3-[4-(2,3-dihydro-1,4-benzo-dioxin-6-ylmethoxy)-phenyl]propionic acid,
- (2S)-2-(1,3-benzoxazol-2-ylamino)-3-[4-(3,5-dimethyl-isoxazol-4-yl)methoxy)phenyl]-propionic acid,
- (2S)-2-(1,3-benzoxazol-2-ylamino)-3-[4-(2-[(cyclohexyl-carbonyl)-(methyl)amino]-ethoxy) phenyl]propionic acid,
- (2S)-2-(1,3-benzoxazol-2-ylamino)-3-[4-(2-[5-methyl-2-(3,4,5-trimethoxyphenyl)-1,3-oxazol-4-yl]ethoxy)phenyl]-propionic acid,
- (2S)-2-(1,3-benzoxazol-2-ylamino)-3-[4-(2-(2tert-butyl-5-methyl-1,3-oxazol-4-yl)-ethoxy) phenyl]propionic acid,
- (2S)-2-(1,3-benzoxazol-2-ylamino)-3-[4-(2-(2-tert-butyl-5-methyl -1,3-oxazol-4-yl)-ethoxy)phenyl]propionic acid,
- (2S)-2-(1,3-benzoxazol-2-ylamino)-3-[4-(2-[cyclohexyl-carbonyl)-(methyl)amino]-thioethoxy) phenyl]propionic acid, and
- (2S)-2-(1,3-benzoxazol-2-ylamino)-3-[4-(2-[(cyclohexyl-carbonyl)-methyl)amino]-ethylmethanesulfony-lamino)-phenyl]-propionic acid, and pharmacuetically acceptable salts thereof.

24. A method of treatment of diseases and conditions mediated by peroxysome proliferator-activated receptor gamma (PPARy) wherein said disease or condition is selected from the group consisting of metabolic syndrome associated disorders, consisting essentially of hypertension, obesity, hyperglycemia and atherosclerosis; insulin resistance; type 2 diabetes; peripheral neuropathy, renal insufficiency, and retinopathy; in a mammal subject in need thereof, said method comprising administration to said mammal a compound of formula (I):

wherein:
W represents COOH;
Y represents NH, N—$C_1$-$C_{10}$-alkyl, O, or S;
Z represents O;
X represents O, S, NH, N—$C_1$-$C_{10}$-alkyl, N-aryl, $NSO_2$—$C_1$-$C_{10}$-alkyl, N—$SO_2$-aryl, or $NSO_2$-heteroaryl;
each of $R_1$ to $R_8$ represents hydrogen atom;
A represents $C_3$-$C_7$-cycloalkyl, halogen-substituted $C_3$-$C_7$-cycloalkyl, aryl, heteroaryl selected from the group consisting of pyrrol-1-yl, pyrrol-2-yl, pyrrol-3-yl, furyl, thienyl, imidazolyl, oxazolyl, thiazolyl, isoxazolyl, 1,2,4-triazolyl, oxadiazolyl, thiadiazolyl, tetrazolyl, pyridinyl, pyrimidinyl, 1,3,5-triazinyl, indolyl, benzo[b]furyl, benzo[b]thienyl, indazolyl, benzimidazolyl, azaindolyl, cynnolyl, isoquinolinyl, and carbazolyl, heterocyclyl, NH—CO—$C_1$-$C_4$-alkyl, —N($C_1$-$C_4$-alkyl)—CO—$C_1$-$C_4$-alkyl, NH—CO-aryl, N($C_1$-$C_4$-alkyl)—CO-aryl, N($C_1$-$C_4$-alkyl)—CO—$C_3$-$C_7$-cycloalkyl, NH—CO—$NH_2$, NH—CO—NH—$C_1$-$C_4$-alkyl, NH—CS—NH—$C_1$-$C_4$-alkyl, NH—CO—NH-aryl, NH—CS—NH-aryl, —$SO_2$—$C_1$-$C_4$-alkyl, —$SO_2$-aryl, or $SO_2$-heteroaryl;
wherein aryl, heteroaryl and heterocyclyl are optionally substituted with one or more substituents independently selected from the group consisting of $C_1$-$C_4$-alkyl, $C_1$-$C_4$-alkoxy, $C_1$-$C_4$-thioalkoxy, ethylene-dioxy, CN, halogen or phenyl, said phenyl being optionally substituted with one or more substituents independently selected from $C_1$-$C_4$-alkyl, $C_1$-$C_4$-alkoxy and halogen atom; and
n represents an integer from 0 to 4, inclusive; and pharmaceutically acceptable salts thereof.

25. The method of claim 5 wherein Y represents N—$CH_3$.
26. The method of claim 8 wherein X represents $NSO_2$—$CH_3$.
27. The method of claim 11 wherein X represents $NSO_2$—$CH_3$.

* * * * *